United States Patent
Rössling et al.

[11] Patent Number: 5,723,146
[45] Date of Patent: Mar. 3, 1998

[54] PHARMACEUTICAL PREPARATIONS

[75] Inventors: Georg Rössling; Andreas Sachse; Jutta Riedl, all of Berlin, Germany

[73] Assignee: Schering Aktiengesellschaft, Berlin, Germany

[21] Appl. No.: 411,392

[22] Filed: Mar. 28, 1995

Related U.S. Application Data

[63] Continuation of Ser. No. 130,539, Oct. 1, 1993, abandoned, and Ser. No. 982,328, Nov. 27, 1992, abandoned, and Ser. No. 857,133, Mar. 25, 1992, abandoned, which is a continuation of Ser. No. 604,021, Oct. 26, 1990, abandoned.

[30] Foreign Application Priority Data

Oct. 27, 1989 [DE] Germany .......... 39 36 328.7

[51] Int. Cl.⁶ .................. A61K 9/127
[52] U.S. Cl. .......... 424/450; 514/859; 514/880
[58] Field of Search ............ 424/450; 514/169, 514/859, 880

[56] References Cited

U.S. PATENT DOCUMENTS

| | | | |
|---|---|---|---|
| 3,728,364 | 4/1973 | Crabbe | 552/647 |
| 4,367,227 | 1/1983 | Bingham | 424/243 |
| 4,396,615 | 8/1983 | Petrow et al. | 424/242 |
| 4,639,440 | 1/1987 | Blandamura | 514/178 |
| 4,731,210 | 3/1988 | Weder | 436/829 |
| 4,882,166 | 11/1989 | Graham et al. | 424/462 |
| 5,094,857 | 3/1992 | Luderschmidt | 424/449 |
| 5,110,904 | 5/1992 | Haviv et al. | 530/313 |

OTHER PUBLICATIONS

Pye, R.J., et al., "Effect of I% cyproterone acetate in Cetomacrogol Cream BPC (Formula A) on sebum excretion rate in patients with acne", British Journal of Dermatology (1976) 95, 427, 26 Mar. 1976.

W.J. Cunliffe et al., "The Effect of Topical Cyproterone Acetate on Sebum Secretion in Patients with Acne," Br. J. Derm., 81:200–201, 1969.

Merk and Dauer, "therapie der androgenetischen Alopezie," Deutsche Apotheker Zeitung (Supplement 10), 128(41):11–15, 1988.

Mezei, Life Science 26, p. 1473, 1980.

Primary Examiner—Gollamudi S. Kishore
Attorney, Agent, or Firm—Millen, White, Zelano, & Branigan, P.C.

[57] ABSTRACT

Pharmaceutical preparations are provided comprising anti-androgenically effective substances encapsulated in liposomes. These preparations are preferably used for topical treatment of androgen-dependent diseases.

9 Claims, No Drawings

PHARMACEUTICAL PREPARATIONS

This application is a continuation of application Ser. No. 08/130,539, filed Oct. 1, 1993, now abandoned; and Ser. No. 07/982,328, filed Nov. 27, 1992, previously abandoned; and Ser. No. 07/857,133, filed Mar. 25, 1992, also abandoned, which is a continuation of Ser. No. 07/604,021 filed Oct. 26, 1990, now abandoned.

BACKGROUND OF THE INVENTION

Pharmaceutical preparations which contain antiandrogenically effective substances have been used to treat androgen-dependent conditions, e.g., diseases in women, such as, for example, acne, seborrhea, androgen-dependent alopecia, and hirsutism. The commercially available preparations used in the Federal Republic of Germany for this purpose contain cyproterone acetate or chlormadinone acetate as an antiandrogenically active ingredient and are administered orally. Because such antiandrogenic preparations have been conventionally employed systematically, they must not be used for treatment during pregnancy or for treatment of men who suffer from androgen-dependent conditions, e.g., diseases, such as seborrhea or androgen-dependent alopecia. With respect to this limiting of applicability and the side effects of the orally administered preparations, there is a need to provide preparations containing antiandrogenically active ingredients which show a good effectiveness by topical application.

SUMMARY OF THE INVENTION

The present invention provides pharmaceutical preparations, comprising antiandrogenically effective substances encapsulated in liposomes. These preparations are prepared preferably in the form of a lotion, a gel or an ointment and are used especially for topical treatment of androgen-dependent diseases.

Upon further study of the specification and appended claims, further objects and advantages of this invention will become apparent to those skilled in the art.

It has now been found that a therapeutically sufficient and uniform rate of penetration of the antiandrogenic active ingredients through the skin surprisingly is achieved if the ingredients are encapsulated in liposomes. Thus, it is possible to provide topically applicable preparations, which show their action basically on the peripheral androgen receptors in the area of application. As a result, systemic side effects are avoided or minimized. Since the active ingredient is concentrated in the liposomes, it is possible to use small amounts of the active ingredient and still achieve a high active ingredient concentration at the site of action. Without wishing to be bound by theory, it is believed that much higher concentrations of antiandrogen can be achieved in the corium and connective tissue of the skin using the pharmaceutical preparations of this invention. In addition, a further advantage of these preparations is that the liposomally encapsulated antiandrogenic active materials are given off over a prolonged period (sustained release).

As active ingredients, the preparations according to the invention can contain both antiandrogenically-effective steroids and nonsteroids with antiandrogenic effectiveness. Suitable nonsteroids are, for example, cimetidine or ketoconazole. Suitable steroids are, among others, spironolactone, chlormadinone acetate or a 5α-reductase inhibitor, such as 1-diethyl-4-methyl-3-oxo-4-aza-5α-androstane-17β-carboxamide, (5 α, 2OR)-4-diaza-21-hydroxy-20-methyl-pregnan-3-one or (4R)-5,10-seco-19-norpregna-4,5-diene-3,10,20-trione. Especially suitable antiandrogenically effective steroids are those which are described in U.S. Pat. Nos. 3,234,093, 4,344,941, 4,456,620, 4,558,041, 4,565,600 and 4,673,673. In a preferred embodiment, topical pharmaceutical preparations of this invention, contain cyproterone acetate (=21-acetoxy-6-chloro-1,2α-methylene-4,6-pregnadiene-3,20-dione) or 17α-propyl mesterolone (=17β-hydroxy-1α-methyl-17α-n-propyl-5α-androstane-3-one) as an active ingredient.

Suitable substances forming liposomes are especially phospholipids, such as sphingomyelins, plasmalogens, phosphatidylcholines, phosphatidylethanolamines, phosphatidylserines, phosphatidylinosites and cardiolipins or also mixtures of these lipids (Dr. Otto-Albert Neumueller: Roempps Chemie-Lexikon: Franck'sche Verlagshandlung Stuttgart (DE) 2665, 3159, 3920 and 4045) and mixtures of these phospholipids with cholesterol and/or charge carriers such as, for example, stearyl amine, stearic acid or dicetyl phosphate. In this case, preferably 0.1 to 40 percent by weight and especially 1 to 20 percent by weight of phospholipid or a mixture is used in relation to the aqueous phase. Advantageous mixtures contain about up to 60 percent by weight of cholesterol and up to 15 percent by weight of charge carrier. Preferred particle sizes for the liposomes are, e.g., from 30–3,000 nm. As solvent for the phospholipids or mixtures and active ingredients, preferably methanol, ethanol, isopropanol, diethyl ether, acetone, chloroform and mixtures of these solvents are used.

Since the lipids are sensitive to oxidation, the process suitably is performed under an inert gas atmosphere, such as nitrogen or argon, and the aqueous liposome solution obtained is stabilized by the addition of antioxidants, such as sodium ascorbate, tocopherol or sodium hydrogen sulfite.

The aqueous liposome solutions can further contain additional auxiliary agents, such as bactericides, preservatives, buffer substances or also active ingredients to produce combination preparations. Such combination preparations are, for example, those which in addition also contain corticoids, such as, for example, hydrocortisone, fluocortolone, difluocortolone, methyl prednisolone and their esters such as methyl prednisolone aceponate.

Processes for encapsulating the active ingredients in liposomes can be used which are well known to one skilled in the art. Thus, for example, the substances forming antiandrogenic active ingredients and liposomes can be dissolved in an organic solvent, the solution can be put into an aqueous phase and optionally after homogenization the solvent can be removed by distillation. Usually, 5 to 100 times the weight of the substance forming liposomes is used per gram of active ingredient.

Thus, for example, the encapsulation of the antiandrogenically active ingredients in liposomes can be performed under the same conditions as the previously known processes of this type (Pharmazie in unserer Zeit [Pharmaceutics in Our Time] 11, 1982, 97–108, Pure Appl. Chem., 53, 1981, 2241–2254). The process for encapsulation of the antiandrogenically active materials is suitable both for the production of multilamellar liposomes and for the production of unilamellar liposomes.

On the other hand, however, it is also possible in the process according to the invention to remove the solvent not by distillation but by other known separation processes, e.g., by transmembrane distillation (Chem. Ing. Techn. [Chem. Eng. Techn.] 56, 1984, 514–521; J. of Membrane Sci., 39, 1988, 25–42; DE-A 33 12 359) and pervaporation (Swiss Chem. 10, 1988, 45–51; ACS Symposium 281, 1985, 467–478; Chem. Ing. Tech. [Chem. Eng. Tech.] 60, 1988, 590–603).

The liposome suspensions containing active ingredients thus produced can, if required, be diluted with water and/or mixed with thickeners, such as hydroxyethyl cellulose, methyl cellulose, Aerosil® (manufacturer Degussa AG, De-6000 Frankfurt), Carbopol® (B. F. Goodrich Chem., USA 44131 Cleveland/Ohio), etc. to produce easily spreadable gels.

Conversely, it is also possible, for example, to concentrate the suspensions by evaporation to dryness by freeze-drying and to work the residue obtained into an ointment base or a cream according to methods conventional to one of ordinary skill in the galenic art.

Although topical applications are preferred, it is also possible to administer the pharmaceutical preparations comprising an antiandrogenically-effective substance encapsulated in liposomes by other than topical routes of administration, e.g., for enteral or parenteral use, according to conventional pharmacological methods.

Preferred compositions are those which can only by applied by topical administration, i.e., they are not useable by, e.g., enteral or parenteral modes of administration. As preferred liquids, creams or pastes, they have viscosities higher than any vehicles used for injection, e.g., higher than water or parenteral oily vehicles. Likewise, such liquids, creams or pastes do not contain a sweetener.

The optimal concentration of active ingredient in the finished pharmaceutical preparations is a function of the type of active ingredient and the galenic preparation and must be determined in the individual case by the usual preliminary experiments. In general, the topical pharmaceutical preparations of this invention contain between about 0.001 to 3 mg and preferably 0.01 to 2.0 mg of the antiandrogenic active ingredient per gram of the preparation.

Particular dosages for a given indication route of administration patent and compound can be routinely determined by using standard pharmaceutical procedures.

The following embodiments are used to explain the invention in more detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding German application P 39 36 328.7, filed Oct. 27, 1989, are hereby incorporated by reference.

EXAMPLES

Example 1

(Film method with subsequent high-pressure homogenization.)

2.0 g of PC S 100 (manufacturer Lipoid KG, DE-Ludwigshafen), 0.2 g of cholesterol and 50 mg of 17α-propyl mesterolone are dissolved in 100 ml of 95% ethanol. Then, the solution is evaporated to dryness in a 500 ml round-bottom flask in a rotary evaporator, and a lipid film is formed on the glass wall. This lipid film is dissolved with 100 ml of twice distilled water. Then, the liposome suspension obtained is homogenized with a high-pressure homogenizer (Microfluidizer®, of Microfluid Corp., USA) at 400 MPa and 25° C. and filtered through a filter of 0.2 micron.

The liposome suspension obtained contains liposomes with an average size of 93 nm. The content of phosphatidylcholine is around 19.2 mg/ml; the content of encapsulated active ingredient is 0.46 mg/ml.

Example 2

(A modified reversed phase evaporation method.)

2.5 g of PC E 100 (manufacturer Lipoid KG, De-Ludwigshafen) and 0.2 g of cyproterone acetate are dissolved in 100 ml of diethyl ether. To this is added 50 ml of 0.015 M aqueous tris-HCl buffer (pH 7.4) and the two-phase mixture is homogenized in a high-pressure homogenizer (Microfluidizer® of Microfluid Corp., USA) at 20 MPa and 25° C. The resulting emulsion is freed from diethyl ether in a rotary evaporator at 4000 Pa and 23° C. and filtered through a filter of 0.45 micron.

The liposome suspension obtained contains liposomes with an average size of 250 nm. The content of phosphatidylcholine is around 48 mg/ml; the content of encapsulated active ingredient is 1.1 mg/ml.

Examples 3 and 4

(Production of a liposomal hydrogel)

The liposome suspensions produced according to examples 1 and 2 are mixed with 0.18% of p-hydroxybenzyl methyl ester and 0.02 of p-hydroxybenzyl propyl ester and 2% of hydroxyethyl cellulose and stirred for 5 minutes at 600 rpm and then briefly at 3000 rpm. Then the mixtures are allowed to sit for 24 hours.

The preparations have a medium-soft consistency; the viscosity value is about 30,000 mPa·s. In the preparation, the liposomes are further suspended in the aqueous phase. They are intact, but mechanically immobilized by the bicoherent system and thus are advantageously separated from one another.

Examples 5 and 6

(Production of a liposomal lipogel)

The liposome suspensions produced according to examples 1 and 2 are freeze-dried. The dried liposome cake is crushed with a percussion mill and the resulting powder is triturated in portions with so much of an ointment base, which consists of vaseline which contains 0.02% of 2.6-di-tert-butyl-4-methylphenol (=BHT) as an antioxidant, that the active ingredient concentration is 0.5 mg/g in the finished-ointment.

Example 7

(Production of a combination preparation)

2.0 g of PC S 100 (manufacturer Lipoid KG, DE-Ludwigshafen), 0.2 g of cholesterol and 50 mg of 17α-propyl mesterolone and 25 mg of methyl prednisolone aceponate are dissolved in 100 ml of 95% ethanol. Then, the solution is evaporated to dryness in a 500 ml round-bottom flask on a rotary evaporator, and a lipid film is formed on the glass wall. This lipid film is dissolved with 100 ml of twice distilled water. Then, the liposome suspension obtained is homogenized with a high-pressure homogenizer (Microfluidizer® of Microfluid Corp., USA) at 400 MPa and 25° C. and filtered through a filter of 0.2 micron.

The liposome suspension obtained contains liposomes with an average size of 93 nm. The content of phosphatidylcholine is around 19.2 mg/ml, the content of encapsulated active ingredient is 0.46 mg/ml.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereto, can make various changes and modifications of the invention to adapt it to various usages and conditions.

What is claimed is:

1. A pharmaceutical composition comprising, cyproterone acetate and liposomes, wherein the cyproterone is encapsulated in the liposomes.

2. A pharmaceutical composition according to claim 1, further comprising a corticoid encapsulated in the liposomes.

3. A pharmaceutical composition according to claim 1, comprising 0.0001–3 mg of cyproterone.

4. A method of treating acne, seborrhea, androgen-dependent alopecia, or hirsutism, comprising administering topically an effective amount of a composition according to claim 1.

5. A method of treating acne, seborrhea, androgen-dependent alopecia, or hirsutism, comprising administering an effective amount of a composition according to claim 2.

6. A method of treating acne, seborrhea, androgen-dependent alopecia, or hirsutism, comprising administering an effective amount of a composition according to claim 3.

7. A method of antagonizing androgen receptors, comprising administering an effective amount of a composition according to claim 1.

8. A method of treating acne, comprising administering topically an effective amount of a composition according to claim 1.

9. A method of treating alopecia, comprising administering topically an effective amount of a composition according to claim 1.

* * * * *